(12) United States Patent
Rajagopal et al.

(10) Patent No.: US 8,496,889 B2
(45) Date of Patent: Jul. 30, 2013

(54) MICROFLUIDIC DEVICE FOR SEPARATING AND SORTING PARTICLES IN A FLUID MEDIUM

(75) Inventors: Aditya Rajagopal, Irvine, CA (US); Michael Woods, Torrance, CA (US)

(73) Assignee: California Institute of Technology, Pasadena, CA (US)

( * ) Notice: Subject to any disclaimer, the term of this patent is extended or adjusted under 35 U.S.C. 154(b) by 61 days.

(21) Appl. No.: 13/069,308

(22) Filed: Mar. 22, 2011

(65) Prior Publication Data

US 2011/0236264 A1    Sep. 29, 2011

Related U.S. Application Data

(60) Provisional application No. 61/316,751, filed on Mar. 23, 2010.

(51) Int. Cl.
| | | |
|---|---|---|
| G01N 21/64 | (2006.01) |
| B01D 45/00 | (2006.01) |
| B01D 21/00 | (2006.01) |
| B01D 35/00 | (2006.01) |
| B01D 39/00 | (2006.01) |
| G01N 1/10 | (2006.01) |
| B01L 3/00 | (2006.01) |
| B01L 3/02 | (2006.01) |
| A01F 12/44 | (2006.01) |
| C12M 3/00 | (2006.01) |

(52) U.S. Cl.
USPC ........ 422/534; 422/82.07; 422/502; 422/504; 422/507; 422/513; 422/527; 422/533; 209/132; 435/287.2; 436/180

(58) Field of Classification Search
USPC .............. 422/82.07, 502, 504, 507, 513, 533, 422/534
See application file for complete search history.

(56) References Cited

U.S. PATENT DOCUMENTS

| | | | |
|---|---|---|---|
| 2007/0059781 A1* | 3/2007 | Kapur et al. ................. 435/7.21 |
| 2007/0197900 A1* | 8/2007 | Baudenbacher et al. ..... 600/409 |
| 2008/0255008 A1* | 10/2008 | Hayes et al. .................... 506/39 |
| 2009/0317798 A1* | 12/2009 | Heid et al. ......................... 435/6 |
| 2011/0011781 A1* | 1/2011 | Blankenstein et al. ....... 210/205 |
| 2011/0206576 A1* | 8/2011 | Woudenberg et al. ........ 422/504 |
| 2012/0078531 A1* | 3/2012 | Lo et al. .......................... 702/21 |

OTHER PUBLICATIONS

S.R. Quake et al. From Micro-to Nanofabrication with Soft Materials. Science 290, 1536-1540 (2000).
M.A. Unger, et al. Monolithic Microfabricated Valves and Pumps by Multilayers Soft Lithography. Science 288, 113-116 (2000).
T. Thorsen, et al. Microfluidic Large-Scale Integration. Science 298, 580-584 (2002).

* cited by examiner

Primary Examiner — Bobby Ramdhanie
Assistant Examiner — Jennifer Wecker
(74) Attorney, Agent, or Firm — Steinfl & Bruno, LLP

(57) ABSTRACT

A microfluidic device for separating emulsion solution into separate particles by passing the emulsion solution through a passive filter. The separated particles can then be sorted into separate chambers through active filtering.

51 Claims, 3 Drawing Sheets

MICROFLUIDIC DEVICE FOR SEPARATING AND SORTING PARTICLES IN A FLUID MEDIUM

CROSS REFERENCE TO RELATED APPLICATIONS

The present application claims priority to U.S. Provisional Application No. 61/316,751, filed on Mar. 23, 2010, which is incorporated herein by reference in its entirety.

FIELD

The present disclosure relates to microfluidic devices. Moreover, it relates to microfluidic devices for separating and sorting particles in a fluid medium.

BACKGROUND

Microfluidics refers to the use of soft lithography and replica molding of elastomeric materials in order to form very small scale fluid and control channels. Multilayer microfluidics uses soft lithography and replica molding to form one or more sets of flow and control layers, which are aligned on top of each other in the final device.

An existing method of microfluidic sorting uses fluorescence activated cell sorting (FACS). FACS relies on using a fluorescence detector in combination with an applied electric field to perform the cell sorting task. This technology is too slow for some applications where it is desired to count and sort very large numbers of droplets in a very short time.

SUMMARY

According to a first aspect, a microfluidic device for separating an emulsion is described, the device comprising: a baseplate layer; a flow layer attached to the baseplate layer; a control layer attached to the flow layer, such that the baseplate layer, the flow layer, and the control layer form the microfluidic device; a first section and a second section; a microfluidic channel within the flow layer, the microfluidic channel passing through the first section and the second section, and configured to flow the emulsion therein; a first filter located within the first section, the first filter configured to separate the emulsion into desired particles and undesired particles; and a second filter located within the second section, the second filter configured to sort the desired particles and send each desired particle into a predetermined channel.

According to a second aspect, a method of separating and sorting an emulsion is described, the method comprising: providing the device according to the first aspect; depositing an emulsion solution to the first filter in the first section; filtering the emulsion, wherein the filtering separates the emulsion into desired particles and undesired particles; pumping the desired particles to the second filter; and filtering the desired particles according to a predetermined criteria, wherein the filtering sorts the emulsion into separate bins.

BRIEF DESCRIPTION OF DRAWINGS

The accompanying drawings, which are incorporated into and constitute a part of this specification, illustrate one or more embodiments of the present disclosure and, together with the description of example embodiments, serve to explain the principles and implementations of the disclosure.

DETAILED DESCRIPTION

The present disclosure describes a microfluidic device for sorting droplets in emulsion solutions. While emulsions in larger non-microfluidic scale devices have diffusive properties to consider, emulsions in microfluidic platforms operate in a laminar regime, thereby minimizing diffusion and allowing for sorting and manipulating micron-scale droplets within the emulsion. A sorting system is described, wherein the emulsion particles are first fed into a size-selective filter column. After filtering out the emulsions that are larger than a predetermined size (e.g., 100 um), the non-filtered emulsion droplets can be queued using dimensional sequestering. Finally, a photo-diode array can be used to analyze fluorescent markers on the emulsion particles. The photo-diode array can then be connected to a computer control system so that the fluorescent marker identification information is fed to the computer and actuate a respective control valve, in conjunction with peristaltic fluidic pumps to allow for the sorting of water droplets.

Figure 1:
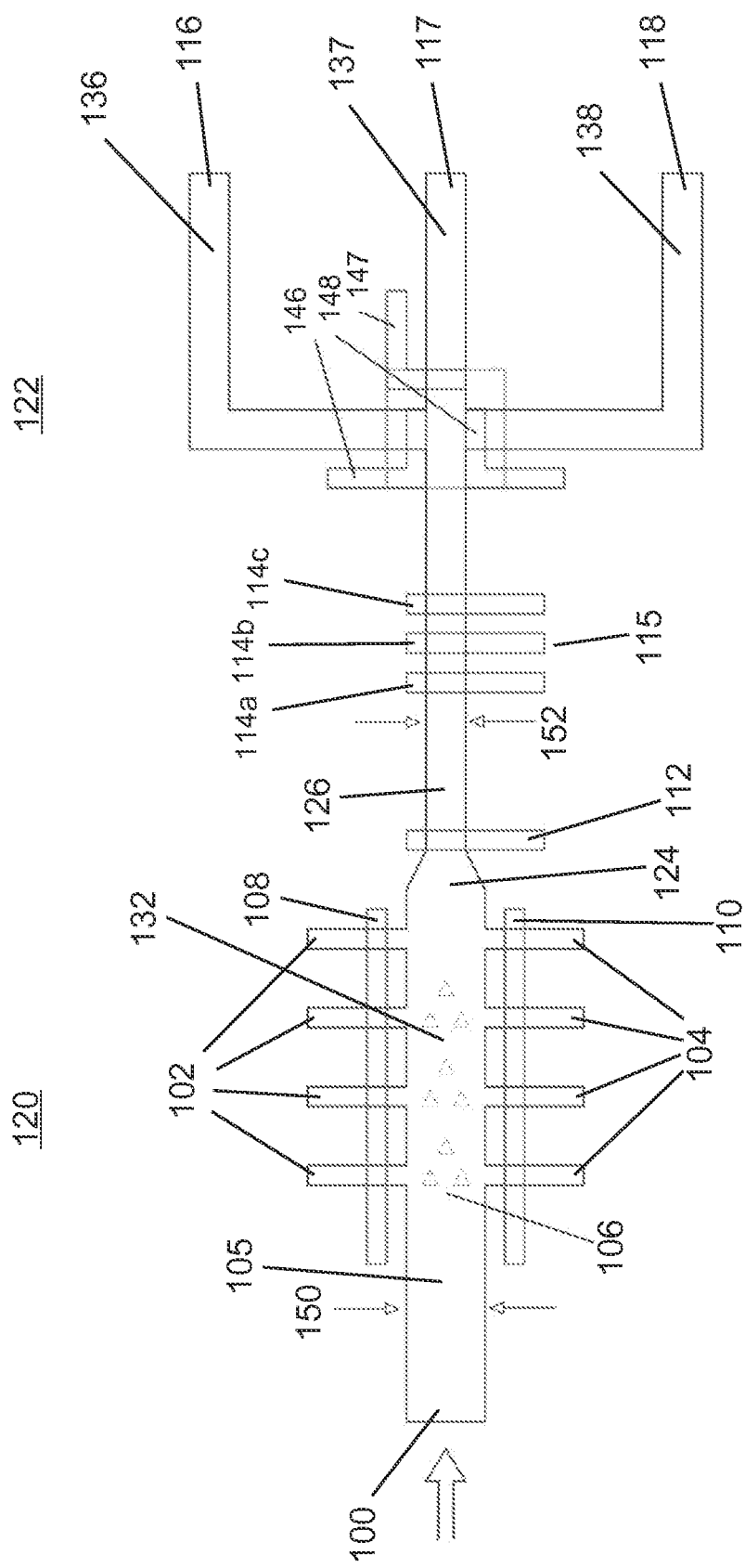
FIG. 1 shows a top view schematic of an exemplary microfluidic particle separating and sorting device.

FIG. 1 shows an overview of an exemplary microfluidic device capable of separating the emulsion into separate elements, and sorting the separated elements into separate bins. Although the emulsion can comprise a variety of combinations of fluids, water-in-oil emulsion solution will be used by way of example and not of limitation, to describe the embodiments herewith. Other examples of emulsion solutions can include blood cells in plasma.

Figure 2:
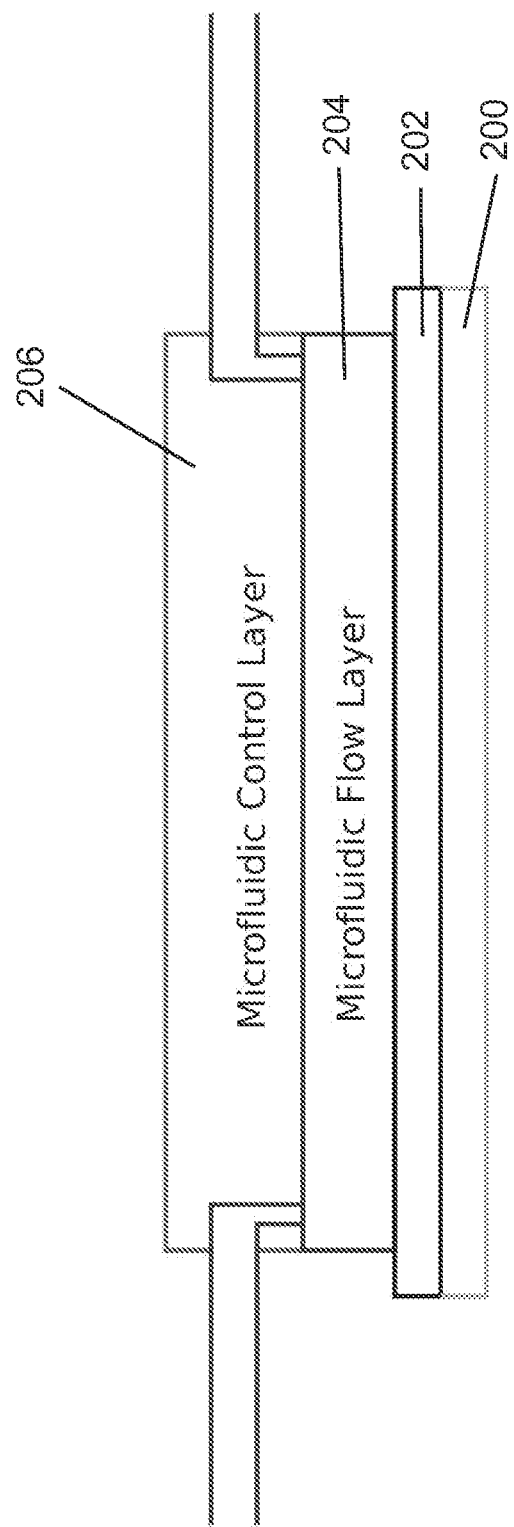
FIG. 2 shows an elevation view schematic of an exemplary microfluidic particle separating and sorting device, specifically showing the layers therein.

The microfluidic device can be built on a single microfluidic chip by using standard semiconductor and polymer fabrication methods. The microfluidic device can comprise four layers, assembled together as shown in FIG. 2.

In one embodiment of the present disclosure, the microfluidic device as shown in FIG. 1 comprises a first section (120) and a second section (122). The first section (120) comprises an emulsion inlet (100) and a first channel (105), and the second section (122) comprises a second channel (126), both of which are configured to allow for the emulsion to flow. The first section (120) and the second section (122) are fluidly connected, with a filter isolation control valve (112) located between the first section (120) and the second section (122). The first section (120) is configured to accept an emulsion deposited at the emulsion inlet (100) by using a positive pressure applying source such as a syringe pump.

In another embodiment of the present disclosure, the first section (120) can comprise an emulsion filtering section (132) for separating the emulsion into the particles comprising the emulsion. The filtering can be performed for example by size, molecular charge, magnetism, chemical, or intermolecular forces, each of which will be described in further details later in this paper. The exemplary device of FIG. 1 is shown with a size and intermolecular force filtering array of wedges (106). The array of wedges (106) are obstructions of a predetermined size (e.g., 100 um), separated by a predetermined distance (e.g., 110 um apart) such that the array of wedges (106) obstruct particles that cannot fit through the space between the wedges. The particles that are able to pass through the space between the wedges flow past the filtering section (132) toward the second section (122).

The filter isolation control valve (112) is located at an outlet (124) of the filtering section (132) to isolate the filtering section (132) from the second channel (126). With the filter isolation control valve (112) opened, emulsion is deposited at the emulsion inlet (100) whereby the positive pressure allows the emulsion to be filtered through the filtering section (132) and flow through the second channel (126), and to the second section (122). Once the emulsion enters the second channel (126), the filter isolation control valve (112) can be shut to isolate the first section (120) from the second section (122). The filter isolation control valve (112) can allow the operator of the device to control an amount of the emulsion components present at the second section (122). By way of example and not of limitation, the channel width (150) of the emulsion inlet (100) and filtering section (132) can be much wider than the channel width (152) of the second section (122) (e.g., 1 mm and 1 um, respectively), thereby allowing the emulsion particles to be queued one-by-one.

In another embodiment, the filtering section (132) further comprises purge inlets (102) with purge inlet control valves (108), and purge exhausts (104) with purge exhaust control valves (110) for removing particles from the filtering section (132). As the emulsion flows through the filtering section (132), the predetermined particles are trapped by the array of wedges (106) as the remaining fluid flows past the array of wedges (106) toward the second section (122). A pressurized source such as compressed air or pressurized fluid (e.g., water, alcohol, solvents, etc.) connected with the purge inlets (102) can be used to remove the trapped particles from the filtering section (132) through the purge outlets (104), thereby cleaning out the filtering section (132).

A peristaltic pump (115) can be located downstream of the filter isolation control valve (112) to pump the emulsion particles from the first section (120) toward the second section (122). The peristaltic pump (115) can be comprised of a bank of pinch valves (114a, 114b, 114c) connected in series and controlled peristaltically by a computer, such that the bank of pinch valves behave as a pump. The passively filtered emulsion particles are pumped to the second section (122) for active filtering. In the second section (122), the emulsion particles are further filtered and sorted into one of the three predetermined sorting exhaust channels (136, 137, 138), each of which are connected to a sorting exhaust bins (116, 117, 118), respectively, for each of the sorting exhaust channels (136, 137, 138).

The microfluidic device described according to various embodiments in the present disclosure can be comprised of four layers. FIG. 2 shows a cross-sectional view of the four layers comprising a control layer (206), a flow layer (204), a glass baseplate layer (202), and a detection layer (200).

Figure 3A:
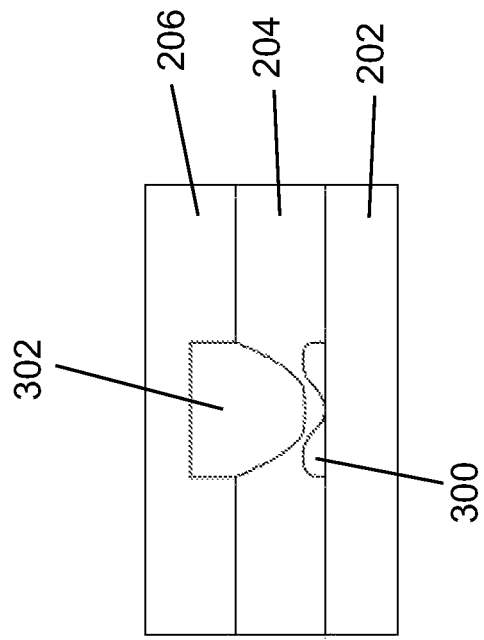
FIG. 3A shows an elevation view schematic of a control layer and a flow layer of an exemplary microfluidic particle separating and sorting device, specifically showing a channel for the fluidic flow and a channel for pressurized air, where the channel is not pressurized.
Figure 3B:
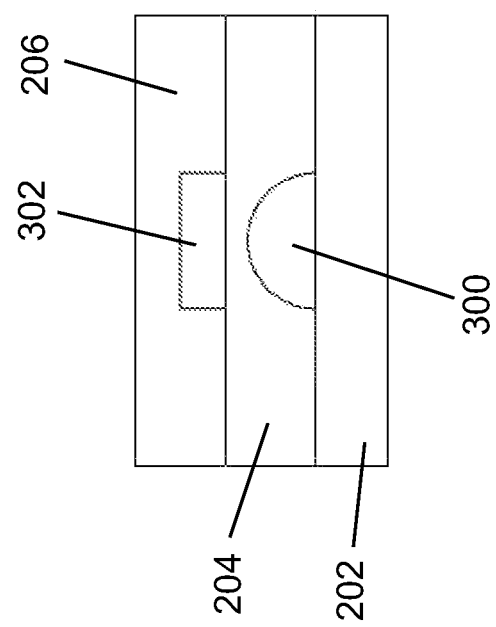
FIG. 3B shows an elevation view schematic of a control layer and a flow layer of an exemplary microfluidic particle separating and sorting device, specifically showing a channel for the fluidic flow and a channel for pressurized air, where the channel is pressurized and thereby deforming the flow layer.

A more detailed cross-sectional view of the microfluidic flow layer (204) is shown in FIGS. 3A-3B comprising a microfluidic channel (300). Such microfluidic channel can (300) represent any of the microfluidic channels shown in FIG. 1 and configured for emulsion flow.

In an embodiment of the present disclosure, the flow layer (204) is made, by way of example and not of limitation, of poly-di-methyl-siloxane (PDMS). The flow layer (204) can be fabricated by the following sequence of steps. First, a replica mold patterned with a mold of the microfluidic channels (300) is made with a thick (e.g., greater than 0.5 um) photo-active polymer (e.g., SU-8 100) using standard photolithographic and electron-beam lithographic exposure methods known in the semiconductor and manufacturing industries. Then, a mixture of PDMS is flowed into the replica mold to create the flow layer (204). Vacuum degassing is performed to remove any gasses from the mixture of PDMS and then thermal treatment is used to harden the PDMS. Once hardened, the flow layer (204) is removed from the mold. The same procedure can be used to manufacture the control layer (206). Although the present disclosure describes the use of PDMS as an example, other elastic materials (e.g., polyimide, kapton, parylene) can be used instead of PDMS.

The control layer (206) is configured to control the flow of emulsion within the microfluidic channels (300) of the flow layer (204) by acting as pinch valves such that the elastic property of the flow layer (204) allows for the flow layer to be deformed to constrict flow of the microfluidic channels (300) as shown in FIG. 3B. The control layer (206) can be manufactured with channels (302) in predetermined locations such that when the control layer (206) is mounted over the flow layer (204), the channels (302) of the control layer (206) align directly over the channels (300) of the flow layer (204). The control layer channels (302) can be connected to a pressure source (e.g., pressurized air) such that when the control layer channel (302) is pressurized, the pressure deforms the flow layer (204) to constrict the flow layer channel (300) and stop flow of the emulsion within that channel.

Similarly, each of the pinch valves (114a, 114b, 114c) shown in FIG. 1 comprising the peristaltic pump (115) can be connected to a pressure source (not shown). The pressure source can be connected to an automated computer system to precisely control the timing sequence of the valves (114a, 114b, 114c) for it to operate as a peristaltic pump (115).

FIGS. 3A-3B show a cross-sectional view of the microfluidic device with the control layer (206) attached to the flow layer (204). The flow layer (204) can be mounted to a clean flat glass-slide platform, forming the foundation of the flow layer channels (300) as the glass baseplate layer (202). Although the glass baseplate layer (202) can be any solid, and flat material that is capable of being foundation, transparent glass allows for visual or optical interrogation of the contents within the channel (i.e., emulsion particles).

In yet another embodiment shown in FIG. 2, the detector layer (200) can comprise a plurality of detectors mounted on the glass baseplate layer (202), on a side opposite from the flow layer (204). By way of example and not of limitation, the detectors can be optical detectors such as complementary metal-oxide-semiconductor (CMOS), charge coupled device (CCD) arrays, and avalanche photodiode (APD). In particular, the detectors can be positioned in the detector layer (200) of the second section (122) as part of the active filtering system to detect fluorescent markers on the emulsion particles. The detectors can be connected to a computer to analyze the detected fluorescent markers. The computer can be further connected together with the pressure system for the pinch valves and the peristaltic pump (115) such that the valves open and close according to the fluorescent marker analysis performed by the computer.

As the emulsion particles are pumped by the peristaltic pump (115) in FIG. 1 toward the second section (122), sorting channel exhaust control valves (146, 147, 148) control the flow of the emulsion particles to each of the sorting channels (136, 137, 138). According to the emulsion particle detected by the fluorescent markers, a respective sorting channel exhaust control valve (146, 147, or 148) that is selected by the computer opens, while the remaining sorting channel exhaust control valves remain shut, thereby releasing the emulsion particles into the desired sorting bins (116, 117, 118). Although FIG. 1 shows three sorting exhaust bins, the microfluidic device can be comprised of any number of bins.

The microfluidic device described herein represents a single filtering/sorting chip. However, using standard semiconductor and polymer fabrication techniques, many copies of the device can be built and operated together in parallel to achieve a higher throughput capacity and accuracy, thereby processing large quantities of emulsion solutions.

Although obstructions by an array of wedges were used as passive filters in the first section (120) of the microfluidic device, other passive filtering methods can be used. In the present disclosure, the term 'obstruction' is used generically to refer to any characteristic that serves the purpose of allowing some portion of, or components of a sampled fluid to pass through the passive filtering region without causing a material change in the portion of, or components of the fluid thusly passed. Examples of passive filtering characteristics can include:

Size—microfluidic channels in the passive filtering region can comprise obstructions designed to only allow passage to particles within a fluid of certain maximum size.

Charge—microfluidic channels in the passive filtering region can comprise charged obstructions, designed to only allow passage to particles of a certain (positive or negative) charge polarity.

Magnetism—microfluidic channels in the passive filtering region can comprise an obstruction applying a magnetic field across the channel. Such field can cause ferromagnetic components within the fluid to align themselves with the field and accelerate forward while diamagnetic components of the fluid are repelled. Thus, magnetic chi can be used as selection criteria for sorting.

Chemical—microfluidic channels in the passive filtering region can comprise an obstruction exhibiting some defined surface chemistry capable of bonding to and capturing some components of the fluid while allowing other components to pass.

Intermolecular forces—microfluidic channels in the passive filtering region can comprise an obstruction with surface exhibiting tendencies towards a particular kind of intermolecular force (e.g., hydrogen bonding, etc.). The obstruction would then be capable of capturing components of the fluid that were susceptible to that force, while allowing the rest of the fluid and its remaining components to pass.

Similarly, although fluorescence detectors were described in the second section (122) of the present disclosure, other active filtering methods can also be used. Examples of active filtering can include:

Fluorescence—electronic device layer beneath the active filtering region can comprise both an LED and photodiode or related electronics, such that the fluid components in the active filtering region can be exposed to light of a certain wavelength that is designed to stimulate emission (and subsequent detection) of light of another wavelength based on the presence of fluorescent markers within the fluid components. Complex applications can use a plurality of markers and a plurality of light sources/detectors, each of which can be optimized towards activating or detecting presence of a particular marker.

Spectrography—electronic device layer can be duplicated on top of and beneath the active filtering region such that one of the device layers can comprise a light source while the other can comprise a light detector. Filtering may then be accomplished on a basis of observing absorbed/transmitted wavelengths of light through the fluid and its components.

Magnetic moment—active filtering region can comprise a magnetic field source, such that the presence (and strength) or absence of a magnetic dipole moment can be determined for any fluid components within the active filtering region.

Charge—active filtering region can comprise a device for determining the polarity and magnitude of electric charge for any fluid components within the active filtering region.

Radioactivity—active filtering region can comprise a device for detecting the radioactive decay and/or half-life associated with any fluid components within the active filtering region.

Resistance/Conductance/Capacitance—active filtering region can comprise a device for determining the resistance, conductance, capacitance or other associated electrical properties of any fluid components within the active filtering region.

Mass—active filtering region might can comprise a device for determining the mass (e.g., by resonance of a mechanical oscillator or other methods) of any fluid components within the active filtering region.

Shape—active filtering region can comprise a device for determining the shape of any fluid components within the active filtering region.

Chemical—active filtering region can comprise a mechanism for exposing components of the fluid to various chemicals in order to determine their reactivities.

Mass chromatography—active filtering region can comprise a device that is capable of applying an electric field across the active filtering region in order to induce the various components of the sampled fluid to accelerate to a terminal velocity along the microfluidic channel. The components of the fluid will naturally separate out by differing masses since such mass differences give rise to differing terminal velocities. Once the electric field is removed, the active filtering region will contain a stratified dispersion of the fluid components by mass.

Although a water-in-oil emulsion was used as an example to describe the microfluidic device of the present disclosure, the microfluidic device can be extended for myriad of applications, including but not limited to devices for controllable drug deliver, chemical content assay, pathogen identification, and blood or serum analysis. For example, the device can use biochemical filters to filter out selected biological and organic compounds. In particular, an ELISA-type immunoassay filter can be used to selectively remove pathogens (e.g., HIV, H1b, etc.) from blood analyte. Such pathogens can then be sorted and binned for quantification. Similar methods can be applied to sort cells according to geometry, mass, or surface proteins.

Although specific elements such were used to describe the various features and embodiments of the present disclosure, a person or ordinary skill in the art would understand that other elements can be used in place.

The examples set forth above are provided to give those of ordinary skill in the art a complete disclosure and description of how to make and use the embodiments of the microfluidic particle sorting device of the disclosure, and are not intended to limit the scope of what the inventors regard as their disclosure. Modifications of the above-described modes for carrying out the disclosure may be used by persons of skill in the art, and are intended to be within the scope of the following claims. All patents and publications mentioned in the specification may be indicative of the levels of skill of those skilled in the art to which the disclosure pertains. All references cited in this disclosure are incorporated by reference to the same extent as if each reference had been incorporated by reference in its entirety individually.

It is to be understood that the disclosure is not limited to particular methods or systems, which can, of course, vary. It is also to be understood that the terminology used herein is for the purpose of describing particular embodiments only, and is not intended to be limiting. As used in this specification and the appended claims, the singular forms "a," "an," and "the" include plural referents unless the content clearly dictates otherwise. The term "plurality" includes two or more referents unless the content clearly dictates otherwise. Unless defined otherwise, all technical and scientific terms used herein have the same meaning as commonly understood by one of ordinary skill in the art to which the disclosure pertains.

A number of embodiments of the disclosure have been described. Nevertheless, it will be understood that various modifications may be made without departing from the spirit and scope of the present disclosure. Accordingly, other embodiments are within the scope of the following claims.

The invention claimed is:

1. A microfluidic device for separating an emulsion, comprising:
   a baseplate layer;
   a flow layer attached to the baseplate layer;
   a control layer attached to the flow layer, such that the baseplate layer, the flow layer, and the control layer form the microfluidic device;
   a first section and a second section;
   a microfluidic channel within the flow layer, the microfluidic channel passing through the first section and the second section, and configured to flow the emulsion therein;
   a first filter located within the first section, the first filter comprising a plurality of obstructions, each obstruction having a predetermined size, and each obstruction separated from a neighboring obstruction by a predetermined separation distance, thereby obstructing particles in the emulsion that cannot fit through spaces in the plurality of obstructions, the obstructed particles comprising undesired particles; and
   a second filter located within the second section, the second filter configured to sort desired particles that pass through the first filter, and send each desired particle into a predetermined channel, wherein the first section further includes a plurality of purge inlets and a plurality of purge outlets adjacent the first filter, configured to remove the undesired particles as a consequence of the first filter.

2. The microfluidic device according to claim 1, wherein the baseplate layer is made of a rigid material.

3. The microfluidic device according to claim 1, wherein the flow layer and the control layer are made of elastic material.

4. The microfluidic device according to claim 3, further comprising a plurality of pressure channels within the control layer, the plurality of the pressure channels configured to be expanded with pressurized air to elastically deform the microfluidic channel within the flow layer, thereby constricting emulsion flow.

5. The microfluidic device according to claim 4, wherein the plurality of pressure channels are configured to operate as pinch valves.

6. The microfluidic device according to claim 1, further comprising a filter isolation control pinch valve between the first section and the second section, the filter isolation control pinch valve configured to control flow of the emulsion from the first section to the second section.

7. The microfluidic device according to claim 1, wherein the plurality of obstructions is an array of wedges, the array of wedges providing filtering of the particles in the emulsion based on particle size and intermolecular force.

8. The microfluidic device according to claim 1, wherein the second filter is selected from the group consisting of: fluorescence filtering, spectrographic filtering, magnetic moment filtering, charge filtering, radioactivity filtering, resistance filtering, conductance filtering, capacitance filtering, mass filtering, shape filtering, chemical filtering, and mass chromatography filtering.

9. The microfluidic device according to claim 1, wherein the baseplate layer is made of glass plate.

10. The microfluidic device according to claim 9, further comprising a plurality of photo-diode detectors attached to the glass baseplate layer on a side opposite the flow layer, wherein the photo-diode detectors detect fluorescent marker particles in the emulsion.

11. The microfluidic device according to claim 10, further comprising a plurality of pinch valves, wherein the plurality of the photo-diode detectors and the pinch valves are connected to a computer system configured to analyze the fluorescent markers of the emulsion particles and open or close a respective pinch valve.

12. The microfluidic device according to claim 1, further comprising a pump configured to pump the emulsion from the first section toward the second section.

13. The microfluidic device according to claim 12, wherein the pump is a peristaltic pump.

14. The microfluidic device according to claim 13, wherein the peristaltic pump is a plurality of pinch valves in series, sequentially controlled by a computer system.

15. The microfluidic device according to claim 1, the second section further comprising a plurality of sorting exhaust channels configured to receive the sorted particles from the second filter, each of the sorting exhaust channels isolated with a pinch valve.

16. The microfluidic device according to claim 1, wherein the undesired particles are removed by connecting a pressure source to the plurality of the purge inlets and applying an air pressure to forcibly remove the undesired particles from the first filter region through the plurality of the purge outlets.

17. A microfluidic system for separating an emulsion, comprising a platform configured to operate a plurality of the microfluidic device according to claim 1 in parallel, thereby increasing emulsion throughput.

18. A method of separating and sorting an emulsion comprising:
   providing the microfluidic device according to claim 1;
   depositing the emulsion in the first section;
   filtering the emulsion, wherein the filtering comprises the first filter separating the emulsion into the desired and undesired particles;
   pumping the desired particles to the second filter; and
   filtering the desired particles according to a predetermined criteria, wherein the filtering sorts the emulsion into separate bins.

19. The method according to claim 18, wherein the pumping is performed with a sequential peristaltic pump.

20. The method according to claim 18, wherein the filtering the desired particles is selected from the group consisting of: fluorescence filtering, spectrographic filtering, magnetic moment filtering, charge filtering, radioactivity filtering, resistance filtering, conductance filtering, capacitance filtering, mass filtering, shape filtering, chemical filtering, and mass chromatography filtering.

21. A microfluidic system for separating an emulsion, comprising a platform configured to operate a plurality of microfluidic devices in parallel, wherein devices of the plurality of microfluidic devices include:
   a baseplate layer;
   a flow layer attached to the baseplate layer;
   a control layer attached to the flow layer, such that the baseplate layer, the flow layer, and the control layer form the microfluidic device;
   a first section and a second section;
   a microfluidic channel within the flow layer, the microfluidic channel passing through the first section and the second section, and configured to flow the emulsion therein;
   a first filter located within the first section, the first filter comprising a plurality of obstructions, each obstruction having a predetermined size, and each obstruction separated from a neighboring obstruction by a predetermined separation distance, thereby obstructing particles in the emulsion that cannot fit through spaces in the plurality of obstructions, the obstructed particles comprising undesired particles; and
   a second filter located within the second section, the second filter configured to sort desired particles that pass through the first filter, and send each desired particle into a predetermined channel, thereby increasing emulsion throughput.

22. The microfluidic system according to claim 21, wherein the baseplate layer is made of a rigid material.

23. The microfluidic system according to claim 21, wherein the flow layer and the control layer are made of elastic material.

24. The microfluidic system according to claim 23, further comprising a plurality of pressure channels within the control layer, the plurality of the pressure channels configured to be expanded with pressurized air to elastically deform the microfluidic channel within the flow layer, thereby constricting emulsion flow.

25. The microfluidic system according to claim 24, wherein the plurality of pressure channels are configured to operate as pinch valves.

26. The microfluidic system according to claim 21, further comprising a filter isolation control pinch valve between the first section and the second section, the filter isolation control pinch valve configured to control flow of the emulsion from the first section to the second section.

27. The microfluidic system according to claim 21, wherein the plurality of obstructions is an array of wedges, the array of wedges providing filtering of the particles in the emulsion based on particle size and intermolecular force.

28. The microfluidic system according to claim 21, wherein the second filter is selected from the group consisting of: fluorescence filtering, spectrographic filtering, magnetic moment filtering, charge filtering, radioactivity filtering, resistance filtering, conductance filtering, capacitance filtering, mass filtering, shape filtering, chemical filtering, and mass chromatography filtering.

29. The microfluidic system according to claim 21, wherein the baseplate layer is made of glass plate.

30. The microfluidic system according to claim 29, further comprising a plurality of photo-diode detectors attached to the glass baseplate layer on a side opposite the flow layer, wherein the photo-diode detectors detect fluorescent marker particles in the emulsion.

31. The microfluidic system according to claim 30, further comprising a plurality of pinch valves, wherein the plurality of the photo-diode detectors and the pinch valves are connected to a computer system configured to analyze the fluorescent markers of the emulsion particles and open or close a respective pinch valve.

32. The microfluidic system according to claim 21, further comprising a pump configured to pump the emulsion from the first section toward the second section.

33. The microfluidic system according to claim 32, wherein the pump is a peristaltic pump.

34. The microfluidic system according to claim 33, wherein the peristaltic pump is a plurality of pinch valves in series, sequentially controlled by a computer system.

35. The microfluidic system according to claim 21, the second section further comprising a plurality of sorting exhaust channels configured to receive the sorted particles from the second filter, each of the sorting exhaust channels isolated with a pinch valve.

36. The microfluidic system according to claim 21, the first section further comprising a plurality of purge inlets and a plurality of purge outlets adjacent the first filter, configured to remove the undesired particles as a consequence of the first filter.

37. The microfluidic system according to claim 36, wherein the undesired particles are removed by connecting a pressure source to the plurality of the purge inlets and applying an air pressure to forcibly remove the undesired particles from the first filter region through the plurality of the purge outlets.

38. A microfluidic device for separating an emulsion, comprising:
   a baseplate layer made of glass plate;
   a flow layer attached to the baseplate layer;
   a plurality of photo-diode detectors attached to the glass baseplate layer on a side opposite the flow layer, wherein the photo-diode detectors detect fluorescent marker particles in the emulsion;
   a control layer attached to the flow layer, such that the baseplate layer, the flow layer, and the control layer form the microfluidic device;
   a first section and a second section;
   a microfluidic channel within the flow layer, the microfluidic channel passing through the first section and the second section, and configured to flow the emulsion therein;
   a plurality of pinch valves, wherein the plurality of the photo-diode detectors and the pinch valves are connected to a computer system configured to analyze the fluorescent markers of the emulsion particles and open or close a respective pinch valve;
   a first filter located within the first section, the first filter comprising a plurality of obstructions, each obstruction having a predetermined size, and each obstruction separated from a neighboring obstruction by a predetermined separation distance, thereby obstructing particles in the emulsion that cannot fit through spaces in the plurality of obstructions, the obstructed particles comprising undesired particles; and
   a second filter located within the second section, the second filter configured to sort desired particles that pass through the first filter, and send each desired particle into a predetermined channel.

39. The microfluidic device according to claim 38, wherein the flow layer and the control layer are made of elastic material.

40. The microfluidic device according to claim 39, further comprising a plurality of pressure channels within the control layer, the plurality of the pressure channels configured to be expanded with pressurized air to elastically deform the microfluidic channel within the flow layer, thereby constricting emulsion flow.

41. The microfluidic device according to claim 40, wherein the plurality of pressure channels is configured to operate the pinch valves.

42. The microfluidic device according to claim 38, further comprising a filter isolation control pinch valve between the first section and the second section, the filter isolation control pinch valve configured to control flow of the emulsion from the first section to the second section.

43. The microfluidic device according to claim 38, wherein the plurality of obstructions is an array of wedges, the array of wedges providing filtering of the particles in the emulsion based on particle size and intermolecular force.

44. The microfluidic device according to claim 38, wherein the second filter is selected from the group consisting of: fluorescence filtering, spectrographic filtering, magnetic moment filtering, charge filtering, radioactivity filtering, resistance filtering, conductance filtering, capacitance filtering, mass filtering, shape filtering, chemical filtering, and mass chromatography filtering.

45. The microfluidic device according to claim 38, wherein the plurality of pinch valves comprise a pump configured to pump the emulsion from the first section toward the second section.

46. The microfluidic device according to claim 38, wherein the second section further comprising a plurality of sorting exhaust channels configured to receive the sorted particles from the second filter, each of the sorting exhaust channels isolated with a pinch valve.

47. The microfluidic device according to claim 38, the first section further comprising a plurality of purge inlets and a plurality of purge outlets adjacent the first filter, configured to remove the undesired particles as a consequence of the first filter.

48. The microfluidic device according to claim 47, wherein the undesired particles are removed by connecting a pressure source to the plurality of the purge inlets and applying an air pressure to forcibly remove the undesired particles from the first filter region through the plurality of the purge outlets.

49. A method of separating and sorting an emulsion comprising:
provciding the microfluidic device according to claim 38;
depositing the emulsion in the first section;
filtering the emulsion, wherein the filtering comprises the first filter separating the emulsion into the desired and undesired particles;
pumping the desired particles to the second filter; and
filtering the desired particles according to a predetermined criteria, wherein the filtering sorts the emulsion into separate bins.

50. The method according to claim 49, wherein the pumping is performed with a sequential peristaltic pump.

51. The method according to claim 49, wherein the filtering the desired particles is selected from the group consisting of: fluorescence filtering, spectrographic filtering, magnetic moment filtering, charge filtering, radioactivity filtering, resistance filtering, conductance filtering, capacitance filtering, mass filtering, shape filtering, chemical filtering, and mass chromatography filtering.

* * * * *